(12) United States Patent
Wu

(10) Patent No.: US 8,529,564 B2
(45) Date of Patent: Sep. 10, 2013

(54) MEDICAL ELECTROCAUTERY INSTRUMENT ASSISTANT DEVICE

(76) Inventor: Jung Wu, Banciao (TW)

( * ) Notice: Subject to any disclaimer, the term of this patent is extended or adjusted under 35 U.S.C. 154(b) by 1094 days.

(21) Appl. No.: 12/232,694

(22) Filed: Sep. 23, 2008

(65) Prior Publication Data

US 2010/0076411 A1    Mar. 25, 2010

(51) Int. Cl.
*A61B 18/18*    (2006.01)

(52) U.S. Cl.
USPC .......................................................... 606/42

(58) Field of Classification Search
USPC ............ 604/540; 606/45, 41, 42, 39; 433/79
See application file for complete search history.

(56) References Cited

U.S. PATENT DOCUMENTS 5,085,657 A * 2/1992 Ben-Simhon .................... 606/42
5,413,575 A * 5/1995 Haenggi ........................ 606/45

* cited by examiner

*Primary Examiner* — Kevin C Sirmons
*Assistant Examiner* — Imani Hayman
(74) *Attorney, Agent, or Firm* — Cheng-Ju Chiang

(57) ABSTRACT

A medical electrocautery instrument assistant device is disclosed including a pump tube, a hollow sleeve tube on an end of the pump tube, and a tube interface on another end of the pump tube and opposite to the hollow sleeve tube. At least a clip is provided between the hollow sleeve tube and the tube interface, each clip forming a position adjusting portion and a clipping portion. Different types of electrocautery instruments remain optimal pump positions relative to the pump tube, drawing out waste blood water and the electrocautery smoke almost entirely, and avoiding hiding operation cuts from view during operations.

6 Claims, 3 Drawing Sheets

MEDICAL ELECTROCAUTERY INSTRUMENT ASSISTANT DEVICE

BACKGROUND OF THE INVENTION

1. Field of the Invention

The present invention relates to an assistant device, and particularly to a medical electrocautery instrument assistant device which is adjustable and ergonomic.

2. Related Art

With development of technology, a variety of new medical technologies are put forth. Traditional medical technologies have some shortcomings, for example, long operation time, and excessive hemorrhage during an operation, which disturb operation process. Electrocautery technology is commonly applied in all kinds of medical operations to obviate the deficiencies above.

An electrocautery instrument assembly comprises an electrocautery machine, an electrocautery instrument for operation, and an assistant device for fixing the electrocautery instrument. The instant invention is mainly involved of the assistant device. As shown in FIG. 1, according to prior art, an assistant device 6 comprises an assembly tube 61, a pump tube 62, rings 631, 632 fixed on the assembly tube 61, and a tube interface 64 provided on ends of the assembly tube 61 and the pump tube 62. The assembly tube 61 positions and abuts against an electrocautery instrument 7. The assembly tube 61 and the pump tube 62 are integrally formed in parallel for providing a path of evacuating out waste blood water and electrocautery smoke. The rings 631, 632 are respectively provided on opposite sides of the assembly tube 61 for assembling and positioning the electrocautery instrument. The tube interface 64 is used to assemble a flexible medical tube.

This assistant device of the prior art has the following deficiencies in use:

1. be not free to operate. The electrocautery instrument 7 has a certain thickness. The assembly tube 61 and the pump tube 62 increase the overall thickness, which is not ergonomic for holding. The assembly of the electrocautery instrument, the assembly tube 61 and the pump tube 62 forms an irregular shape, making surgeons not free to operate precisely. Based on this, on some aspects, visual scope may be limited during operations.

2. waste blood water and electrocautery smoke can not be dissipated effectively. The rings 631, 632 are fixed on both ends of the assembly tube 61, and can not match for the electrocautery instruments of different operations. Furthermore, when the electrocautery instrument 7 is assembled on the assembly tube 61, an electrocautery bistoury 70 on a front of the electrocautery instrument 7 can not remain an appropriate position and angle. The electrocautery bistoury 70 extends much beyond the pump tube 62, and can not suck out waste blood water and electrocautery smoke sufficiently, thereby hiding operation cuts from view.

SUMMARY OF THE INVENTION

Accordingly, an object of the present invention is to provide a medical electrocautery instrument assistant device which is held ergonomically and is adjusted freely, whereby an electrocautery bistoury of an electrocautery instrument is retained an appropriate position for sufficiently drawing out waste blood water and electrocautery smoke, and operation cuts are not hidden from view.

The medical electrocautery instrument assistant device according to the present invention comprises a pump tube and a hollow sleeve tube on an end of the pump tube. The hollow sleeve tube includes a support portion adapted for supporting an electrocautery instrument. A tube interface is provided on another end of the pump tube and opposite to the hollow sleeve tube. At least a clip is provided between the hollow sleeve tube and the tube interface, each clip forming a position adjusting portion and a clipping portion. In this way, different types of electrocautery instruments remain optimal pump positions relative to the pump tube, drawing out waste blood water and the electrocautery smoke almost entirely, and avoiding hiding operation cuts from view during operations.

DESCRIPTION OF THE PREFERRED EMBODIMENTS

Figure 1:
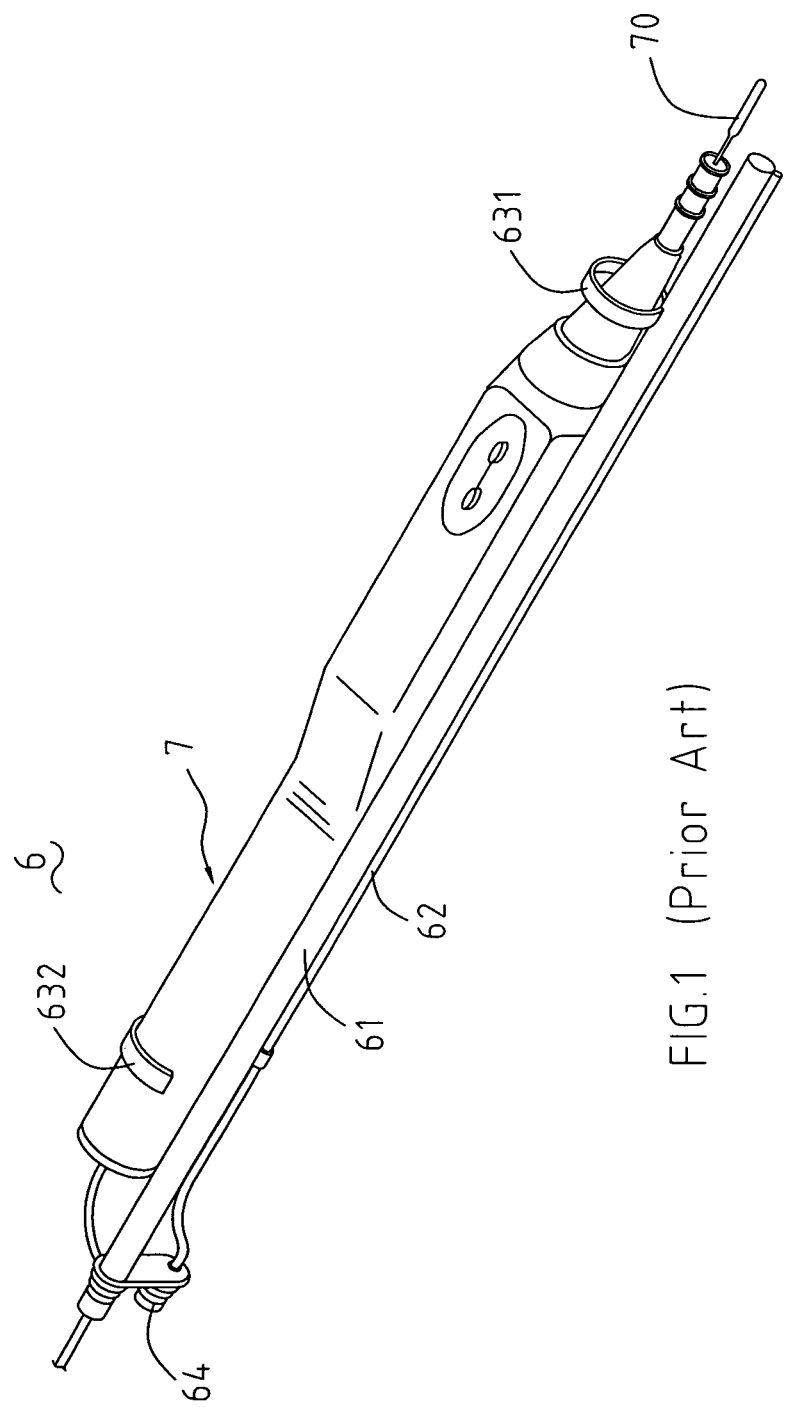
FIG. 1 is a perspective view of a medical electrocautery instrument assistant device according to prior art.
Figure 2:
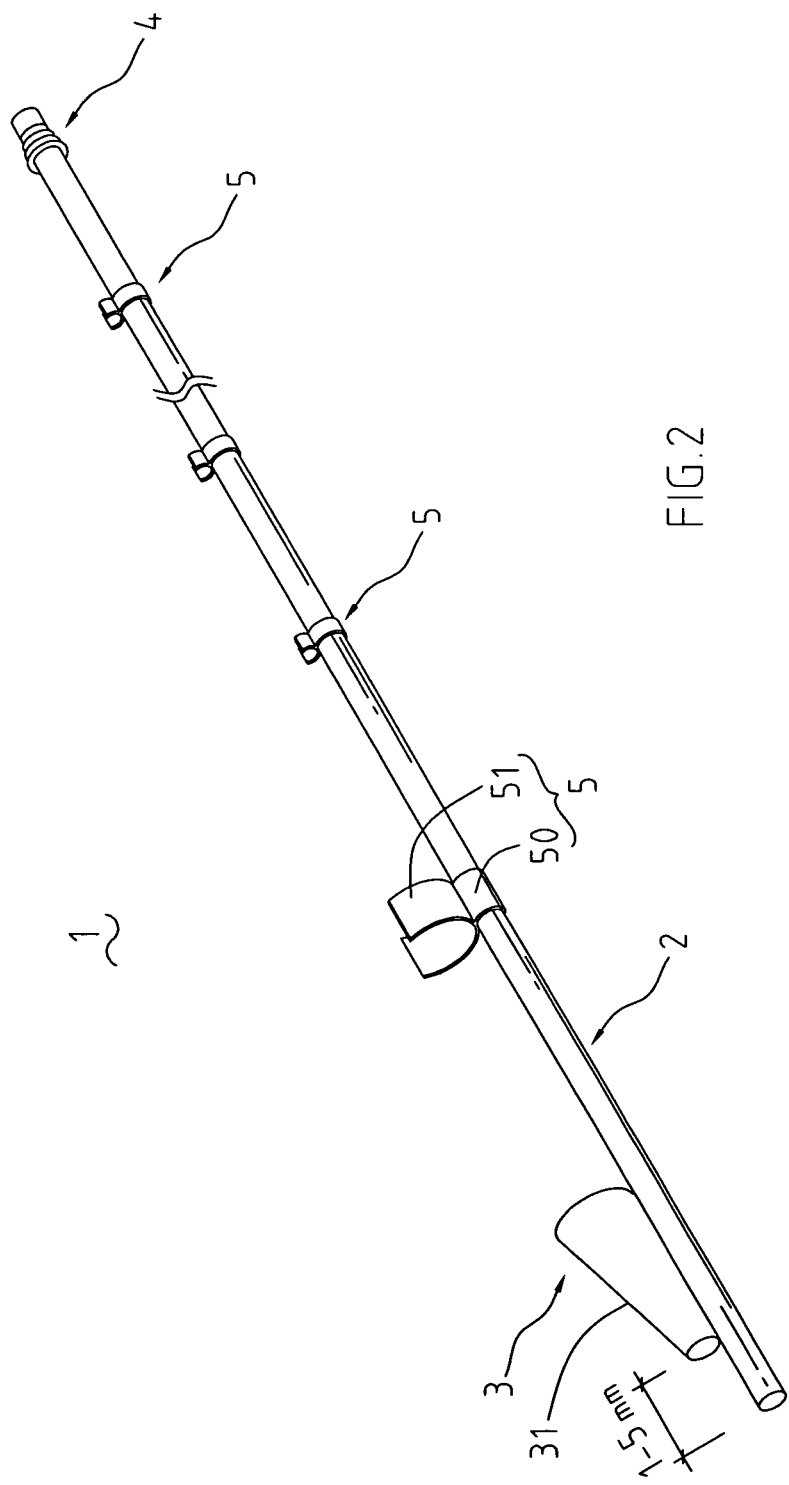
FIG. 2 is a perspective view of a medical electrocautery instrument assistant device according to the present invention.

With reference to FIG. 2, a medical electrocautery instrument assistant device 1 in accordance with the present invention comprises a pump tube 2 and a hollow sleeve tube 3 on an end of the pump tube 2. The pump tube 2 is a flexible medical tube. The hollow sleeve tube 3 is unitarily formed with the pump tube 2, and includes a support portion 31 for supporting an electrocautery instrument 7 (shown in FIG. 3). The support portion 31 is conic or upright for matching for the electrocautery instrument 7, thereby being held ergonomically by hands. In this embodiment, the support portion 31 is conic. A tube interface 4 is provided on another end of the pump tube 2 and opposite to the hollow sleeve tube 3 for connecting with other tubes. A plurality of clips 5 are provided between the hollow sleeve tube 3 and the tube interface 4. Each clip 5 forms a position adjusting portion 50 for adjusting positions thereof, and a clipping portion 51 for clamping the electrocautery instrument 7. The position adjusting portion 50 is a lock ring which has an inner diameter approximately equal to an outer diameter of the pump tube 2 in such a way that the position adjusting portion 50 is retainable on the pump tube 2 by tightly fitting and is movable with respect to the pump tube 2. Each clipping portion 51 is C-shaped to form a gap therein to enable the clipping portion 51 to be expandable laterally, whereby the electrocautery instrument 7 is detachably clamped by the clipping portion 51. In this embodiment, four clips 5 are provided. The clip 5 approaching the hollow sleeve tube 3 has a relatively larger clipping portion 51 for holding the electrocautery instrument 7, while other clips 5 have relatively smaller clipping portions 51 for holding a wire 32 of the electrocautery instrument 7, as shown in FIG. 2, avoiding the wire 32 influences an operation. The hollow sleeve tube 3 is defined with a length along a longitudinal direction of the pump tube 2, and the length of the hollow sleeve tube 3 is shorter than a distance between the at least a clip 5 and the end of the pump tube 2 opposite to the tube interface 4. Therefore, the hollow sleeve tube 3 is capable of being entirely disposed between the at least a clip 5 and the end of the pump tube 2 opposite to the tube interface 4 along the longitudinal direction of the pump tube 2.

Figure 3:
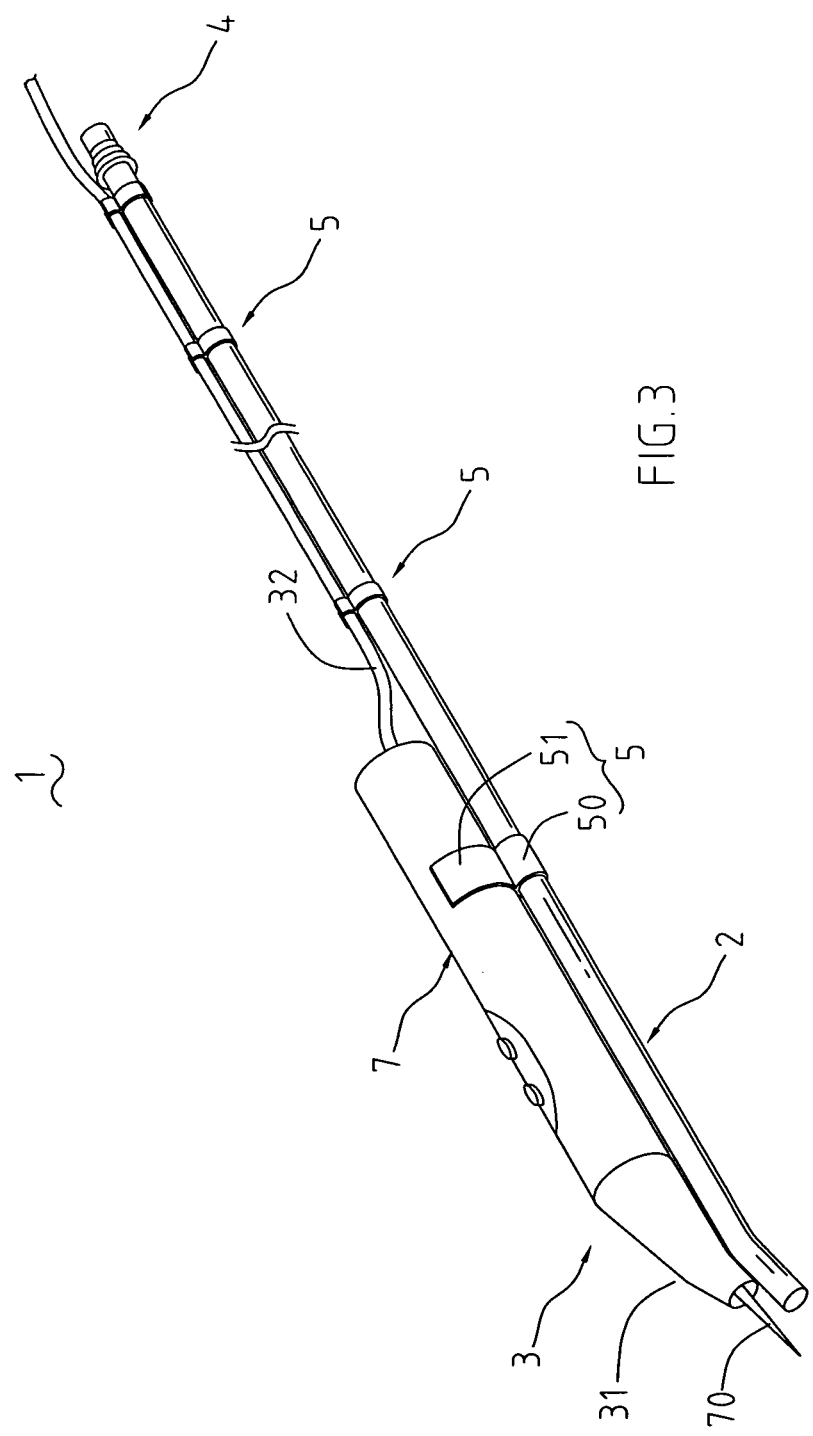
FIG. 3 is a perspective view of medical electrocautery instrument assistant device of FIG. 2 being assembled with an electrocautery instrument.

It is noted, as shown in FIG. 3, the clips 5 are respectively adjustable in position. Therefore, in use, regardless of assembly with any electrocautery instrument 7, the electrocautery instrument 7 and the pump tube 2 remain appropriate relative pump positions. In other words, an end of the conic support portion 31 of the hollow sleeve tube 3 is spaced a distance of 1-5 mm apart from an adjacent end of the pump tube 2. Moreover, the end of the pump tube 2 remains below an electrocautery bistoury 70 of the electrocautery instrument 7 for avoiding blocking the electrocautery bistoury 70. Thus the electrocautery bistoury 70 of the electrocautery instrument 7 extends outward appropriate length when assembled on the support portion 31, drawing out waste blood water and the electrocautery smoke almost entirely, and avoiding hiding operation cuts from view during operations.

Therefore, the medical electrocautery instrument assistant device has many advantages. The clips 5 are adjustable respectively for matching for different types of electrocautery instruments, whereby the electrocautery bistoury of the electrocautery instrument is spaced an optimal distance apart from the end of the pump tube 2, and operation cuts are not hidden by waste blood water and the electrocautery smoke. Additionally, the hollow sleeve tube 3 is properly assembled with the electrocautery instrument, which meets ergonomic requirement for facilitating operations.

It is understood that the invention may be embodied in other forms without departing from the spirit thereof. Thus, the present examples and embodiments are to be considered in all respects as illustrative and not restrictive, and the invention is not to be limited to the details given herein.

What is claimed is:

1. A medical electrocautery instrument assistant device comprising:
    a pump tube and a hollow sleeve tube disposed on an end of the pump tube, the hollow sleeve tube including a support portion having a conic shape as a whole adapted for supporting an electrocautery instrument;
    a tube interface being provided on another end of the pump tube and opposite to the hollow sleeve tube; and
    at least a clip being provided between the hollow sleeve tube and the tube interface, each clip having a position adjusting portion and a clipping portion integrally formed on the position adjusting portion;
    wherein the position adjusting portion is fit onto the pump tube, and the clipping portion has a C shape to form a gap therein and to enable the clipping portion to be expandable laterally, whereby the electrocautery instrument is detachably clamped by the clipping portion and remains optimal pump positions relative to the pump tube, drawing out waste blood water and electrocautery smoke, and avoiding hiding operation cuts from view during operations, and wherein the hollow sleeve tube is defined with a predetermined length along a longitudinal direction of the pump tube so that the length of the hollow sleeve tube is shorter than a distance along the longitudinal direction between the at least a clip and the end of the pump tube opposite to the tube interface, and the hollow sleeve tube is entirely disposed between the at least a clip and the end of the pump tube opposite to the tube interface along the longitudinal direction of the pump tube.

2. The medical electrocautery instrument assistant device as claimed in claim 1, wherein the pump tube is a flexible medical tube.

3. The medical electrocautery instrument assistant device as claimed in claim 1, wherein the hollow sleeve tube is unitarily formed with the pump tube.

4. The medical electrocautery instrument assistant device as claimed in claim 1, wherein the electrocautery instrument and the pump tube remain appropriate relative pump positions in such a way that an end of the support portion of the hollow sleeve tube is spaced a distance of 1-5 mm apart from an end of the pump tube, and that the end of the pump tube remains below an electrocautery bistoury of the electrocautery instrument for avoiding blocking the electrocautery bistoury, the electrocautery bistoury of the electrocautery instrument extending outward appropriate length when assembled on the support portion for facilitating operations.

5. The medical electrocautery instrument assistant device as claimed in claim 1, wherein four clips are provided, the clip approaching the hollow sleeve tube having a relatively larger clipping portion for holding an electrocautery instrument, while other clips having relatively smaller clipping portions for holding a wire of the electrocautery instrument.

6. The medical electrocautery instrument assistant device as claimed in claim 1, wherein the at least a clip is moveable along the pump tube.

* * * * *